US011457930B2

(12) United States Patent
Gagner

(10) Patent No.: US 11,457,930 B2
(45) Date of Patent: Oct. 4, 2022

(54) ENHANCED TECHNIQUES FOR INSERTION AND EXTRACTION OF A BOUGIE DURING GASTROPLASTY

(71) Applicant: BALLAST MEDICAL INC., Montreal (CA)

(72) Inventor: Michel Gagner, Montreal (CA)

(73) Assignee: BALLAST MEDICAL INC., Québec (CA)

( * ) Notice: Subject to any disclaimer, the term of this patent is extended or adjusted under 35 U.S.C. 154(b) by 133 days.

(21) Appl. No.: 17/054,827

(22) PCT Filed: May 15, 2019

(86) PCT No.: PCT/CA2019/050656
§ 371 (c)(1),
(2) Date: Nov. 12, 2020

(87) PCT Pub. No.: WO2019/218066
PCT Pub. Date: Nov. 21, 2019

(65) Prior Publication Data
US 2021/0212696 A1     Jul. 15, 2021

Related U.S. Application Data

(60) Provisional application No. 62/671,713, filed on May 15, 2018.

(51) Int. Cl.
*A61B 17/128* (2006.01)
*A61B 17/00* (2006.01)

(52) U.S. Cl.
CPC ............ *A61B 17/1285* (2013.01); *A61B 2017/00336* (2013.01); *A61B 2017/00818* (2013.01);
(Continued)

(58) Field of Classification Search
CPC ...... A61B 17/1285; A61B 2017/00292; A61B 2017/00336; A61B 2017/00818;
(Continued)

(56) References Cited

U.S. PATENT DOCUMENTS 7,918,869 B2 * 4/2011 Saadat ............... A61B 17/1285
606/153
8,449,560 B2 * 5/2013 Roth .................. A61B 17/29
606/139
(Continued)

FOREIGN PATENT DOCUMENTS

WO     2009097585 A1    8/2009

OTHER PUBLICATIONS

International Search Report and Written Opinion dated Jul. 25, 2019 for corresponding International Application No. PCT/CA2019/050656 (Authorized officer, Alan Jones), 10 pages.

*Primary Examiner* — Ryan J. Severson
(74) *Attorney, Agent, or Firm* — MH2 Technology Law Group, LLP

(57) ABSTRACT

An assembly including a bougie and a sheath for use in performing a gastroplasty for dividing a stomach of a patient into a sleeve receiving food and a bypass portion. The bougie includes an elongated body having a segment being shaped to follow a lesser curve of the stomach, and an extension member being movable within the stomach for positioning a distal portion thereof away from a gastroesophageal junction of the stomach and to define a fluid passage between the sleeve and the bypass portion. The sheath has an elongated main lumen in which the bougie is inserted and the sheath is translatable along the bougie to selectively expose the extension member of the bougie to
(Continued)

FIG. 2 perform its guiding action, or hide the extension member to ensure secure displacement of the bougie within the stomach and along the oesophagus.

20 Claims, 18 Drawing Sheets

(52) U.S. Cl.
CPC .............. *A61B 2017/00876* (2013.01); *A61B 2217/005* (2013.01)

(58) Field of Classification Search
CPC ..... A61B 2017/00876; A61B 2217/005; A61F 5/0003; A61F 5/0036; A61F 5/0083; A61F 5/0086; A61F 5/0089
See application file for complete search history.

(56) References Cited

U.S. PATENT DOCUMENTS

| | | | |
|---|---|---|---|
| 8,663,149 B2 | 3/2014 | Gagner et al. | |
| 8,702,734 B2* | 4/2014 | Kraemer | A61B 17/068 606/151 |
| 9,549,737 B2 | 1/2017 | Gagner et al. | |
| 9,603,735 B2* | 3/2017 | Trivedi | A61B 17/00234 |
| 9,615,952 B2* | 4/2017 | Scott | A61F 5/0086 |
| 9,655,758 B2* | 5/2017 | Miesse | A61B 17/29 |
| 9,801,748 B2* | 10/2017 | Dierking | A61B 90/30 |
| 9,808,368 B2* | 11/2017 | Radi | A61B 17/07207 |
| 10,159,425 B2* | 12/2018 | Marczyk | A61B 5/065 |
| 10,271,865 B2* | 4/2019 | Trivedi | A61F 5/0083 |
| 10,433,997 B2* | 10/2019 | Gagner | A61F 5/0083 |
| 10,478,326 B2* | 11/2019 | Miesse | A61B 17/22 |
| 10,898,361 B2* | 1/2021 | Nocca | A61F 5/0089 |
| 10,959,746 B2* | 3/2021 | Trivedi | A61F 5/0083 |
| 2005/0251158 A1* | 11/2005 | Saadat | A61B 17/1285 606/153 |
| 2007/0167960 A1 | 7/2007 | Roth et al. | |
| 2011/0178454 A1* | 7/2011 | Gagner | A61B 17/07207 604/9 |
| 2011/0213390 A1* | 9/2011 | Kraemer | A61B 17/07207 606/153 |
| 2013/0165774 A1* | 6/2013 | Nocca | A61M 25/1002 600/431 |
| 2014/0018722 A1 | 1/2014 | Scott et al. | |
| 2014/0114121 A1* | 4/2014 | Trivedi | A61B 17/00234 600/37 |
| 2014/0155918 A1* | 6/2014 | Gagner | A61F 5/0083 606/153 |
| 2015/0133740 A1* | 5/2015 | Dierking | A61B 90/30 600/249 |
| 2015/0133771 A1 | 5/2015 | Maraczyk et al. | |
| 2015/0133772 A1 | 5/2015 | Miesse et al. | |
| 2017/0079823 A1 | 3/2017 | Gagner et al. | |
| 2017/0246019 A1* | 8/2017 | Miesse | A61B 17/30 |
| 2018/0049902 A1* | 2/2018 | Dierking | A61F 5/0076 |
| 2019/0117114 A1* | 4/2019 | Marczyk | A61B 5/065 |
| 2020/0054471 A1* | 2/2020 | Gagner | A61B 17/07207 |
| 2021/0212696 A1* | 7/2021 | Gagner | A61B 17/07207 |
| 2022/0079577 A1* | 3/2022 | Bar-On | A61B 17/0487 |

* cited by examiner

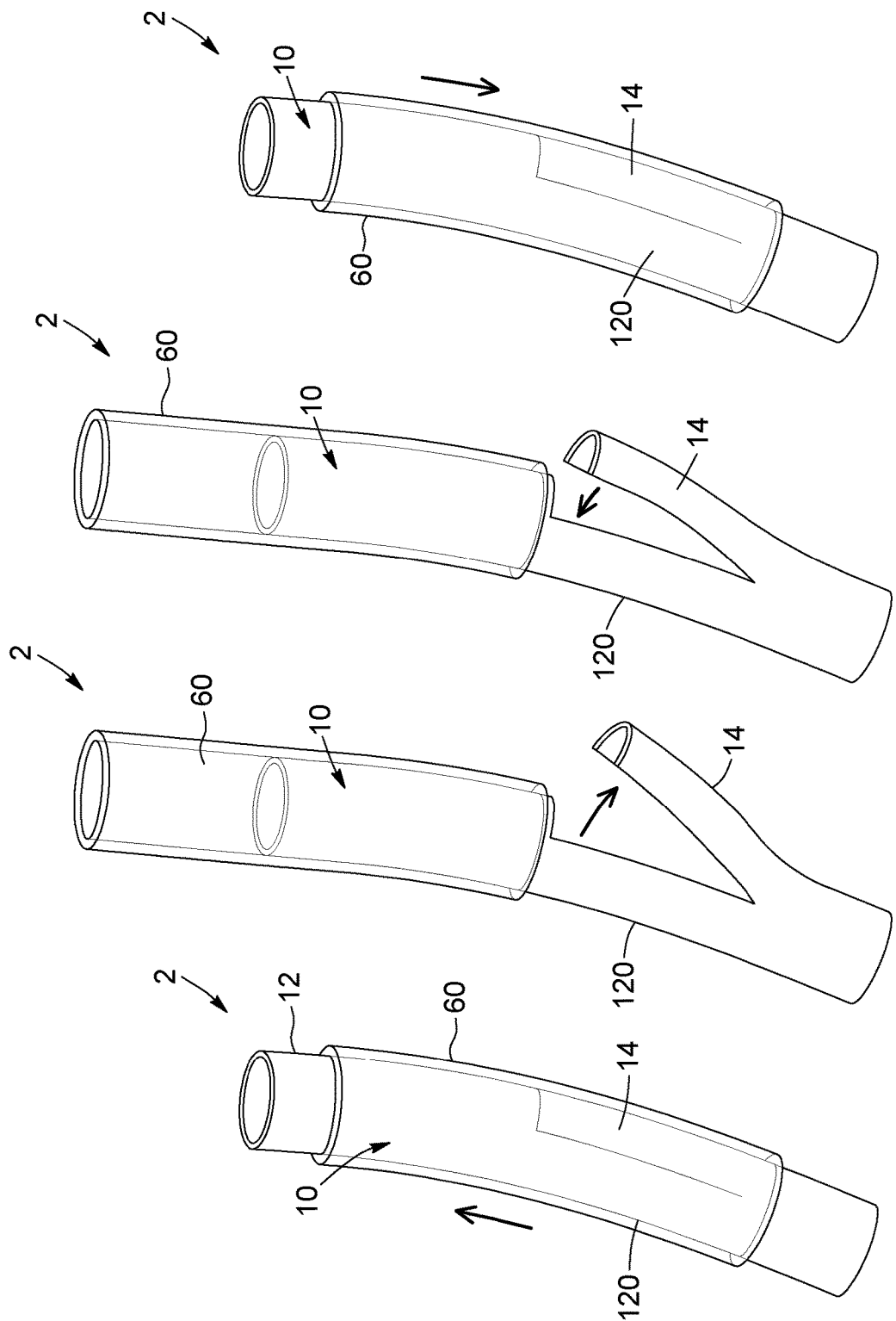

ENHANCED TECHNIQUES FOR INSERTION AND EXTRACTION OF A BOUGIE DURING GASTROPLASTY

CROSS-REFERENCE TO RELATED APPLICATIONS

This application is a U.S. National Stage application of PCT/CA2019/050656 filed 15 May 2019, which claims priority to U.S. Provisional Patent Application No. 62/671,713 filed 15 May 2018, the entire disclosures of which are incorporated herein by reference.

TECHNICAL FIELD

The present techniques generally relate to the field of gastroplasty, and more particularly to implementations of an assembly and related methods for insertion and extraction of such assembly into and from the stomach of a patient.

BACKGROUND

Many health care experts consider obesity the largest health problem facing westernized societies and considered obesity an epidemic. From a medical standpoint, obesity is the primary risk factor for type 2 diabetes and obstructive sleep apnea. It increases the chances for heart disease, pulmonary disease, infertility, osteoarthritis, cholecystitis and several major cancers, including breast and colon cancers. Despite these alarming facts, treatment options for obesity remain limited.

Treatment options include surgical procedures that restrict the size of the stomach and/or bypass parts of the intestine. These surgical procedures are the only remedies that provide lasting weight loss for the majority of morbidly obese individuals.

Bariatric surgery is a treatment for morbid obesity that involves alteration of a patient's digestive tract to encourage weight loss and to help maintain normal weight. Known bariatric surgery procedures include jejuno-ileal bypass, jejuno-colic shunt, biliopancreatic diversion, gastric bypass, Roux-en-Y gastric bypass, gastroplasty, gastric banding, vertical banded gastroplasty, and silastic ring gastroplasty. A more complete history of bariatric surgery can be found on the website of the American Society for Bariatric Surgery at http://www.asbs.org.

Advances in laparoscopic surgery have also allowed physicians to perform operations that previously required an invasive and painful access incision to be made. For example, in the case of a sleeve gastrectomy, the surgeon can suture the stomach together, forming a stoma, using a bougie as a guide along the lesser curvature of the stomach. A bougie is a relatively simple, solid tube inserted into the stomach via the esophagus. The surgeon sutures the stomach shut around the bougie, such that the stoma formed matches the size and the narrow, tubular shape of the bougie.

Certain bougies, as described in U.S. Pat. Nos. 8,663,149, 9,549,737 and US Patent Application No. 20170079823, are designed to further guide the surgeon during a sleeve gastroplasty. The bougie includes an extension member which reversibly splays in an extended position and at an angle away from the main body of the bougie within the stomach. Such extension member is used as a guide for stapling the stomach away from a gastroesophageal junction thereof when forming the sleeve, while providing an open end to the formed sleeve to evacuate fluids that tend to accumulate within the isolated portion of the stomach.

There is still a need for mechanisms providing further guidance to the surgeon during insertion of the bougie within the stomach, size reduction of the stomach into a sleeve and extraction of the bougie from the formed sleeve, thereby reducing the risks to damage the stomach tissues and nerves.

SUMMARY

In one aspect, there is provided an assembly for use in performing a gastroplasty for dividing a stomach of a patient into a sleeve receiving food and a bypass portion. The assembly includes a bougie configured to enter the stomach. The bougie includes an elongated body having a segment being shaped to follow a lesser curve of the stomach, and an extension member having a proximal portion connected to the segment of the elongate body. The extension member is movable from a retracted position in which the extension member is generally aligned with the elongate body, to an extended position in which the extension member extends at an angle away from the segment within the stomach for positioning a distal portion of the extension member away from a gastroesophageal junction of the stomach. The assembly further includes a sheath having an elongated main lumen in which the bougie is inserted. The sheath is translatable along the bougie between:
  a first position in which the sheath at least covers the extension member of the bougie for maintaining the extension member in the retracted position, and
  a second position in which the sheath is staggered with respect to the extension member for allowing the extension member to move from the retracted position into the extended position.

In some implementations, the assembly further includes an actuator which is configured to displace the sheath between the first position and the second position along the bougie. The assembly may also include an activation mechanism which is configured to move the extension member from at least one of the retracted position and the extended position into to the other position.

In some implementations of the assembly, a distal portion of the extension member is a free-end that is spaced-away from a proximal portion of the segment to define a Y-shape when the extension member is in the extended position.

In other implementations of the assembly, a distal portion of the extension member is a free-end that is spaced-away from a distal portion of the segment to define a T-shape when the extension member is in the extended position.

In other implementations of the assembly, a distal portion of the extension member is a free-end that is spaced-away from a distal end of the segment to define a L-shape when the extension member is in the extended position.

The sheath can include a polymeric material. In some implementations, the sheath has a proximal portion made of a first material and a distal portion made of a second material, the second material having an enhanced rigidity in comparison to the first material, said distal portion enclosing the extension member of the bougie in the retracted position when the sheath is in the first position.

In some implementations of the assembly, the bougie further includes a suction lumen extending along the elongated body, the suction lumen being connectable to a suction source and being in fluid communication with the stomach cavity via at least one aperture of the elongated body. Optionally, the elongated body is provided with a plurality of apertures located in a distal portion of the elongated body to allow fluid passage from the stomach into the suction lumen when a suction power is applied. Further optionally, the assembly includes an air valve having an opening in fluid communication with the suction lumen, the valve being connected to a proximal portion of the elongated body.

In some implementations of the assembly, a plurality of light-emitting elements is distributed along at least a portion of the bougie to provide further visible guidance when joining the stomach walls to form the sleeve.

In another aspect, there is provided a sheathing device for guiding insertion and extraction of a bougie into and from a stomach during a sleeve gastroplasty. The sheathing device includes a tubular body having a main elongated lumen for slidably receiving the bougie therein. The tubular body is translatable with respect to the bougie between:
- a first position in which the tubular body at least covers a guiding segment of the bougie during insertion and extraction of the guiding segment into and from the stomach, and
- a second position in which the tubular body is staggered with respect to the guiding segment for allowing the guiding segment to serve as guide to form a sleeve within the stomach.

In some implementations, the sheathing device includes an actuator which is configured to displace the tubular body between the first position and the second position along the bougie.

In some implementations, the tubular body is made of a material which is flexible enough to bend according to the movements of the bougie. Optionally, the tubular body includes or is made of a polymeric material. Further optionally, the tubular body has a proximal portion made of a first material and a distal portion made of a second material, the second material having an enhanced rigidity in comparison to the first material, said distal portion enclosing the guiding segment of the bougie when the tubular body is in the first position.

In some implementations, the tubular body comprises distal and proximal tube segments, the proximal tube segment being translatable with respect to the bougie in a backward direction to expose the guiding segment, and the distal tube segment being translatable with respect to the bougie in a forward direction to hide the guiding segment.

In some implementations, the actuator is a wire system comprising at least one wire which is pullable to actuate translation of the sheathing device with respect to the bougie.

In some implementations, the at least one wire is at least partially integrated within a wall of the tubular body.

The sheathing device of any one of claims 19 to 23, wherein the tubular body extends along the bougie from the stomach and further along the oesophagus so as to be actuated from an oral cavity of a patient.

In another aspect, there is provided a kit for performing a gastroplasty dividing a stomach of a patient into a sleeve receiving food and a bypass portion. The kit includes a bougie configured to enter the stomach, and a sheath having an elongated main lumen in which the bougie is slidably insertable. The bougie includes an elongated body having a segment being shaped to follow a lesser curve of the stomach, and an extension member having a proximal portion connected to the segment of the elongate body, the extension member being movable from a retracted position in which the extension member is generally aligned with the elongate body, to an extended position in which the extension member extends at an angle away from the segment within the stomach for positioning a distal portion of the extension member away from a gastroesophageal junction of the stomach. The sheath is translatable along the bougie between:
- a first position in which the sheath at least covers the extension member of the bougie for maintaining the extension member in the retracted position, and
- a second position in which the sheath is staggered with respect to the extension member for allowing the extension member to move from the retracted position into the extended position.

In some implementations, the kit includes an actuator which is configured to displace the sheath between the first position and the second position along the bougie. Optionally, the kit also includes an activation mechanism which is configured to move the extension member from at least one of the retracted position and the extended position into to the other position.

In some implementations, the bougie further includes a suction lumen extending along the elongated body, the suction lumen being connectable to a suction source and being in fluid communication with at least one aperture of the elongated body. Optionally, the elongated body is provided with a plurality of apertures located in a distal portion of the elongated body to allow fluid passage from the stomach into the suction lumen when a suction power is applied.

In some implementations, the kit includes a plurality of light-emitting elements positionable along at least a portion of the bougie to provide further visible guidance when joining the stomach walls to form the sleeve.

In another aspect, there is provided a method of performing a sleeve gastroplasty using an assembly comprising a bougie having a guiding segment for forming the sleeve and a sheath for securing the guiding segment. The method includes:
- inserting the bougie into a stomach of a patient until the guiding segment is positioned along a lesser curve of the stomach;
- displacing the sheath with respect to the bougie in a backward direction to expose the guiding segment;
- joining opposed walls of the stomach along a junction line following an inner edge of the guiding segment to form the sleeve within the stomach;
- displacing the sheath with respect to the bougie in a forward direction to cover the guiding segment; and
- removing the bougie from the stomach.

In another aspect, there is provided a method of performing a sleeve gastroplasty using an assembly comprising a bougie having a guiding segment for forming the sleeve and a sheath for securing the guiding segment, the method comprising:
- inserting the bougie into a stomach of a patient until the guiding segment is positioned along a lesser curve of the stomach;
- displacing the sheath with respect to the bougie in a backward direction to expose the guiding segment;
- joining opposed walls of the stomach along a junction line in response to a position of the guiding segment in the stomach to form the sleeve within the stomach;
- displacing the sheath with respect to the bougie in a forward direction to cover the guiding segment; and
- removing the bougie from the stomach.

In some implementations, the method includes extending a portion of the guiding segment outwardly from the lesser curve of the stomach until a distal end of the portion of the guiding segment is located proximal to a gastroesophageal junction, and wherein the joining of the opposed walls of the stomach is performed along an inner edge of the guiding segment until reaching the distal end thereof, thereby defining a fluid passage between the sleeve and a bypass portion in a top region of the stomach.

In other implementations, the method includes extending a portion of the guiding segment outwardly from the lesser curve of the stomach until a distal end of the portion of the guiding segment is located proximal to a gastroduodenal junction, and wherein the joining of the opposed walls of the stomach is performed along an inner edge of the bougie until reaching the distal end thereof, thereby defining a fluid passage between the sleeve and a bypass portion in a distal region of the stomach Optionally, the displacement of the sheath with respect to the bougie in the backward direction to expose the guiding segment actuates the extension of the portion of the guiding segment.

In some implementations, the method includes retracting the portion of the guiding segment in alignment with the lesser curve of the stomach before displacing the sheath with respect to the bougie in the forward direction to cover the guiding segment.

In some implementations, the method includes controlling movement of the portion of the guiding segment with at least one wire or magnet cooperating with the distal end of said portion.

In some implementations, the sheath includes a distal tube segment and a proximal tube segment, and displacing the sheath comprises backward translation of the proximal tube segment to expose the guiding segment, and forward translation of the distal tube segment to hide the guiding segment.

In some implementations, displacing the sheath is performed from an oral cavity of the patient by direct pushing and/or pulling of a wire system operatively connected to the sheath.

Optionally, displacing the sheath is performed from an oral cavity of the patient by direct pushing or pulling of the sheath itself or of a wire system cooperating with the sheath.

While the invention will be described in conjunction with example embodiments, it will be understood that it is not intended to limit the scope of the invention to such embodiments. On the contrary, it is intended to cover all alternatives, modifications and equivalents as may be included as defined by the present description. The objects, advantages and other features of the present invention will become more apparent and be better understood upon reading of the following non-restrictive description of the invention, given with reference to the accompanying drawings.

BRIEF DESCRIPTION OF THE DRAWINGS

Implementations of the gastroplasty assembly and related method are represented in and will be further understood in connection with the following figures.

FIGS. 1 to 4 are schematic representations of a bougie and related sheath for performing a sleeve gastroplasty illustrating successive displacements of the sheath and extension member of the bougie (Y-shaped structure).

DETAILED DESCRIPTION

Figure 5:
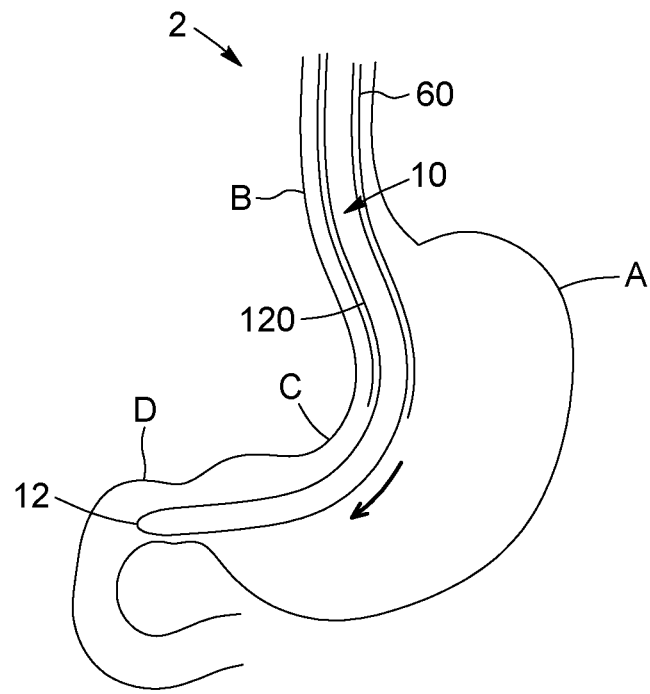
FIG. 5 is a schematic cross-sectional view of a stomach according to a first step of a sleeve gastroplasty method using a gastroplasty assembly, the sleeve being open to a bypass portion of the stomach proximal to a gastro-oesophageal junction thereof.

The present techniques relate to insertion and extraction of a bougie within and from a stomach during a sleeve gastroplasty. Such surgical procedure includes the use of a bougie for guidance during junction of opposed stomach walls to form a sleeve and a bypass portion within the cavity of the stomach.

The bougie includes an extension member which is used as a guide to join the stomach walls away from the gastroesophageal junction, such that the food will be directed into the sleeve instead of the bypassed portion of the stomach. The extension member is movable from a retracted position in which the extension member is generally aligned with an elongated body of the bougie, to an extended position in which the extension member extends at an angle away from said elongated body, to define the shape and size of the sleeve to be formed. Any movement of the extension member between the retracted position and the extended position during insertion or extraction of the bougie into or from the stomach could dangerously damage tissues and nerves.

In one aspect, there is provided a sheath which is configured to cooperate with the bougie and serve as a guide for insertion and extraction of the bougie into and from the stomach. More particularly, the sheath surrounds a segment of the bougie to prevent the extension member of the bougie from splaying during displacement of the bougie along the oesophagus and stomach. The sheath is also translatable with respect to the bougie such that the extension member of the bougie can be freed from the sheath and act as a guide for the formation of the sleeve within the stomach.

In the context of the present description and accompanying figures, it should be noted that the term "backward" or "back" is to be understood as in a proximal direction towards an oral cavity of the patient, and the term "forward" or "forth" is to be understood in opposition to "backward" or "back" as in a distal direction towards a gastroduodenal junction of the stomach.

FIGS. 1 to 4 schematically illustrate a portion of an assembly (2) including a bougie (10) and a sheath (60), the bougie extending through the sheath (60) such that a segment of the bougie (10) is contained within the sheath (60). FIGS. 1 to 4 particularly illustrate the steps resulting from a back and forth translation of the sheath (60) with respect to the bougie (10).

As seen in FIG. 1, the sheath (60) can be positioned along an elongated body (12) of the bougie (10) so as to surround and fully contain at least a segment (120) of the elongated body (12) and an extension member (14) of the bougie. The extension member (14) is in a retracted position wherein said extension member (14) is generally aligned with the elongated body (12). A backward translation movement of the sheath (60) with respect to the bougie (10) can be performed (see arrow in FIG. 1) when the extension member (14) needs to be freed from the sheath (60), as the sheath (60) is translatable with respect to the bougie (10), thereby converting the assembly (2) into the state illustrated in FIG. 2.

Translation of the sheath along the bougie can be performed according to various techniques available to one skilled in the art, including manual actuation from the oral cavity of the patient. The sheath may be sized and configured to extend along the bougie within both stomach and oesophagus, thereby having a length sufficient to be directly accessible to a practitioner from the patient's oral cavity. Alternatively, the sheath may be sized and configured to surround a segment of the bougie, said segment being located within the stomach when the bougie is fully inserted therein. In this implementation, the sheath may cooperate with a wire assembly which is actuable from the patient's oral cavity to induce backward and forward translation of the sheath with respect to the segment of the bougie.

Referring to FIGS. 2 and 3, once the sheath (60) is translated backward along the bougie (12) until the extension member (14) and the corresponding segment (120) of the elongated body (12) of the bougie are uncovered, the extension member (14) can be reversibly moved from the retracted position into an extended position (FIG. 2) in which the extension member (14) extends at an angle away from the segment (120).

Splaying of the extension member into the extended position may be activated according to various techniques as long as the extension member can come back into its retracted position for extraction of the bougie from the stomach.

In some implementations, biasing means may be used to bias the extension member in the extended or retracted position. The extension member has therefore to be sufficiently flexible to change position and also sufficiently resilient to come back to its natural position (retracted or extended) when unbiased.

In other implementations, the extension member may be hingedly connected to a segment of the elongated body of the bougie so as to pivot between the extended position and the retracted position.

In other implementations, a distal portion of the extension member may include a magnetic material, such as a ferromagnetic material, to render the distal portion moveable under the action of a magnet or a magnetized tool. For example, the extension member may be biased in the retracted position and unbiased under the action of a magnet which can pull the distal end of the extension member away from the elongated member of the bougie.

Referring to FIG. 3, the extension member (14) may be moved into the retracted position once said extension member (14) has served its guiding purpose to form a sleeve within the stomach (not illustrated in FIGS. 1 to 4)). Referring to FIG. 4, once the extension member (14) is generally aligned with the elongated body (12), forward translation (see arrow in FIG. 4) of the sheath (60) can be performed until the extension member (14) is fully enclosed within the sheath (60), the sheath (60) preventing the extension member (14) from being freed in the extended position during extraction of the bougie (10) from the stomach.

In another aspect, there is provided a method to perform a sleeve gastroplasty using the assembly of a bougie and a sheath as described herein. Exemplary implementations of the method to perform the sleeve gastroplasty are further illustrated in FIGS. 5 to 9.

Referring to FIG. 5, the method includes introducing the assembly (2) including the bougie (10) and the sheath (60) into the stomach (A) via the esophagus (B). During insertion of the assembly (2), the sheath (60) is positioned with respect to the bougie so as to prevent the extension member (not appearing on FIG. 5) from moving into an extended position during forward displacement (see arrow in FIG. 5) of the elongated body (12) along the oesophagus (B) and into the stomach (A).

As both bougie (10) and sheath (60) are displaced along the oesophagus (B) and the lesser curve (C) of the stomach (A), materials of the bougie (10) and the sheath (60) have mechanical properties conferring enough flexibility to the devices for bending according to the curves of the organs. Optionally, the bougie (10) and the sheath (60) may be curved to facilitate insertion and positioning of the bougie (10) within the stomach (A) along the lesser curve (C) as seen in FIG. 5.

In some implementations, the sheath may be a tubular body made of a polymeric material. Optionally, two different materials may be used to form the tubular body such that the sheath includes a segment of enhanced rigidity, this segment enclosing the extension member of the bougie in the retracted position.

Still referring to FIG. 5, the method includes positioning a distal end of the elongated body (12) of the bougie (10) near a gastro-duodenal junction (D). The sheath (60) is configured to cover at least the segment (120) of the elongated body (12) from which the extension member (not illustrated in FIG. 5) departs.

Figure 6:
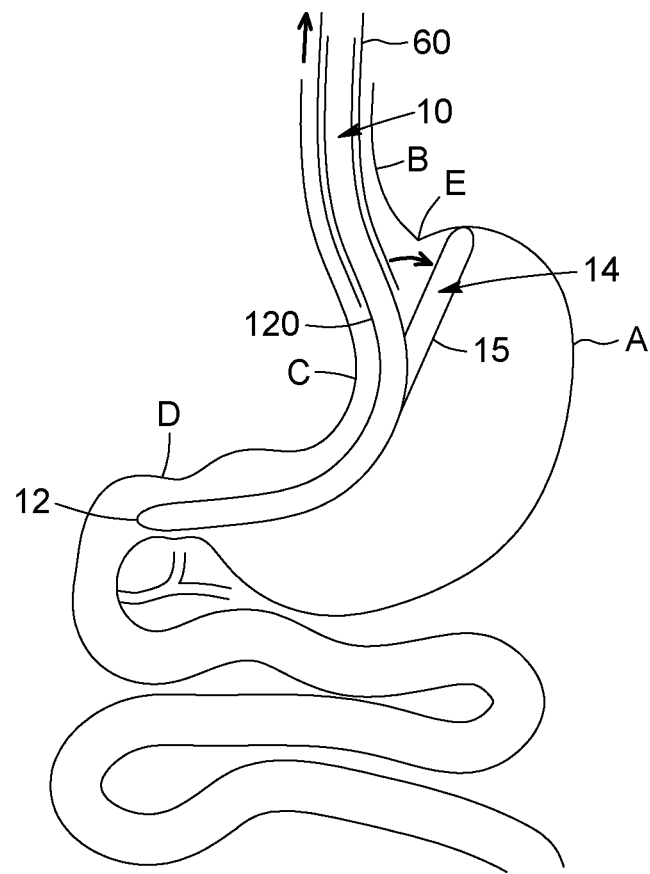
FIG. 6 is a schematic cross-sectional view of a stomach according to a second step of the sleeve gastroplasty method using the gastroplasty assembly.

Referring to FIG. 6, once the bougie (10) is positioned according to FIG. 5, the method includes backward translation of the sheath (60) such that the extension member (14) is at least partially exposed and can be moved into the extended position. Once in the extended position, the extension member (14) extends at an angle away from segment (120) of the elongated body (12). The angle can be chosen such that an inner edge (15) of the extension member (14), opposite the lesser curve (C), is positioned away from the gastroesophageal junction (E).

Figure 20:
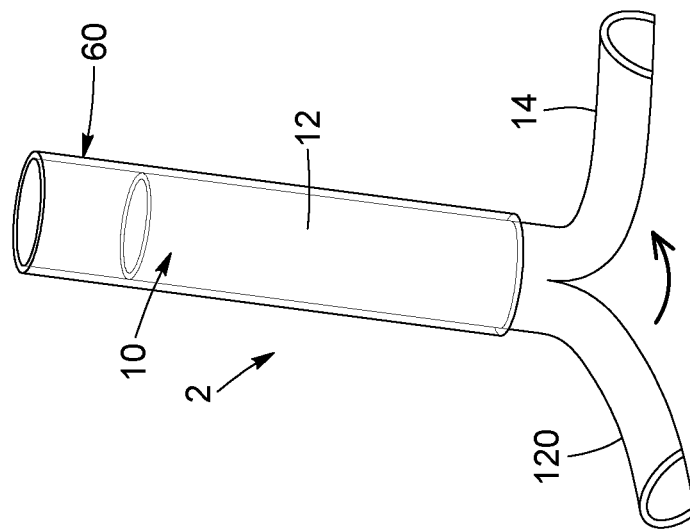
FIGS. 18 to 20 are schematic representations of a bougie and related sheath for performing a sleeve gastroplasty illustrating displacement of the sheath to release a distal extension member of the bougie (T-shaped structure).
Figure 19:
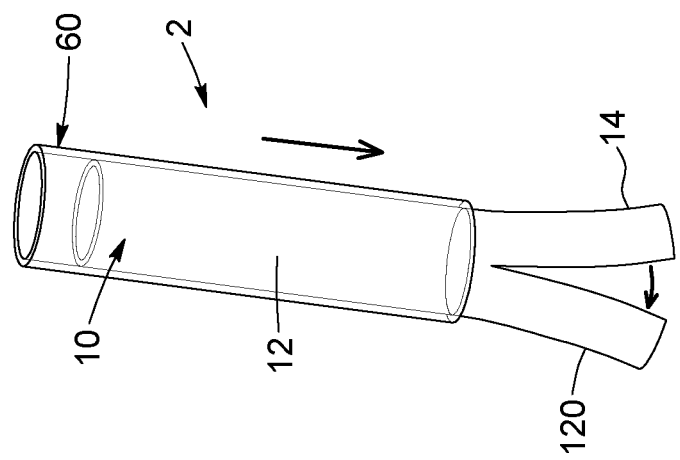
Figure 18:
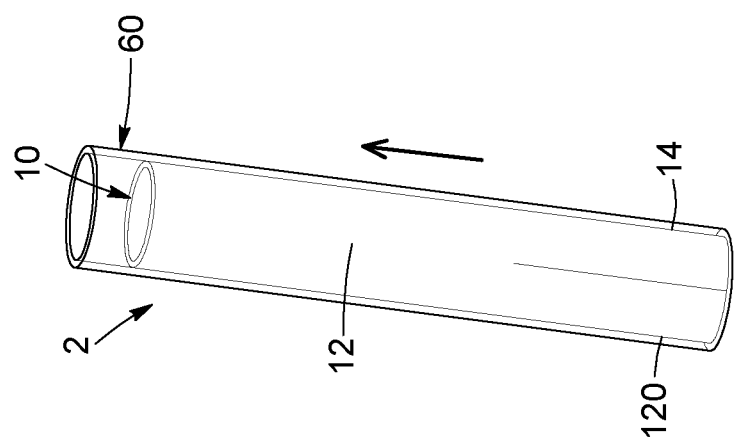

It should be noted that depending on the mechanisms responsible for the movement of the extension member, the method may include actuating the splaying of the extension member into the extended position and the closing of the extension member into the retracted position. As one skilled in the art will readily understand, translation of the sheath with respect to the bougie may be sufficient, in some cases, to lead to the splaying and/or closing of the extension member when the extension member is respectively freed from or contained by the sheath (such as seen in FIGS. 18 to 20). In other cases, an activation mechanism may be used to put the extension member into the extended or retracted position (such as the wire and ring system illustrated in FIGS. 12 and 13). Therefore, the sheath may be sized to accommodate for this activation mechanism of the extension member.

Figure 7:
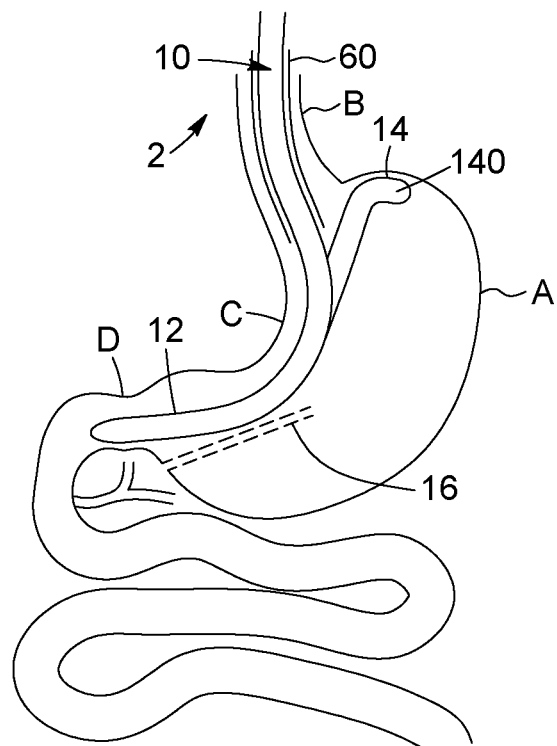
FIG. 7 is a schematic cross-sectional view of a stomach according to a third step of the sleeve gastroplasty method using the gastroplasty assembly.
Figure 8:
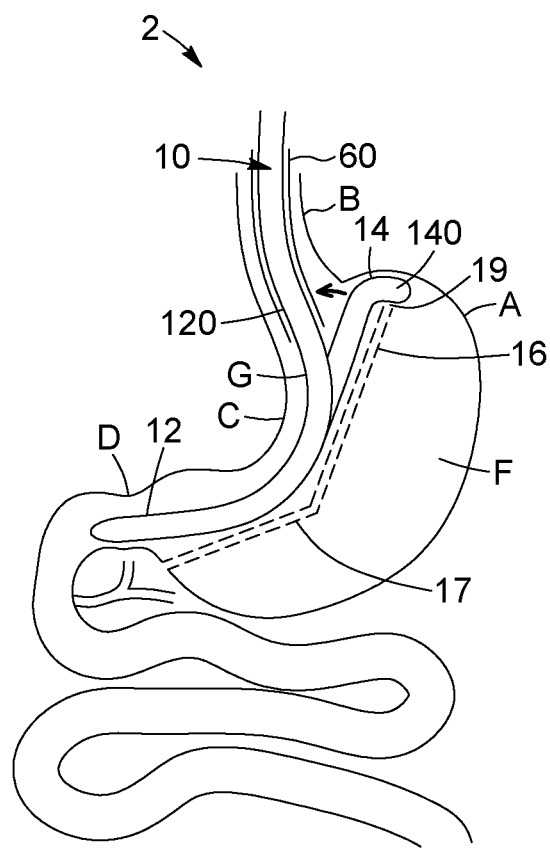
FIG. 8 is a schematic cross-sectional view of a stomach according to a fourth step of the sleeve gastroplasty method using the gastroplasty assembly.

Referring to FIGS. 7 and 8, the method includes forming a sleeve within the stomach (A) including joining opposed stomach walls together along a junction line (16) which follows the inner edge (15) of the distal portion of the bougie (10) and extension member (14) in extended position. The shown junction line (16) begins at the bottom of the stomach (A) and extends up and towards the oesophagus (B). The method further includes leaving a top region (19) of the stomach open such that the junction line (16) ends prior to reaching the top of the stomach (A). The opening in the top region (19) ensures fluid communication between a bypassed portion of the stomach (F) and the newly formed sleeve (G) (also referred to as stoma) as better seen on FIG. 8. Optionally, the fluid passage (19) may have a width of at least one centimeter. The extension member (14) can be configured to be bendable and adapt to the shape of the gastroesophageal junction (D). A distal portion (140) of the extension member (14) can be used as an obstacle to prevent the sleeve being fully closed and to mark the end of the junction line. More specifically, the distal portion (140) of the extension member can be positioned away from the gastroesophageal junction (E) and proximal to the stomach wall, thereby serving to size the opening in the top region (19) of the stomach between the formed sleeve (G) and the bypassed portion of the stomach (F). Such positioning of the distal portion (140) of the extension member thus guides the practitioner in avoiding to fully join stomach walls.

Joining the stomach walls along the junction line may be performed according to various techniques available to one skilled in the art. For example, at least one of suturing, stapling and clamping techniques may be used to join the stomach walls along the bougie according to the junction line and thereby form the sleeve within the stomach. An example of a clamping technique is particularly illustrated in FIG. 14.

Figure 9:
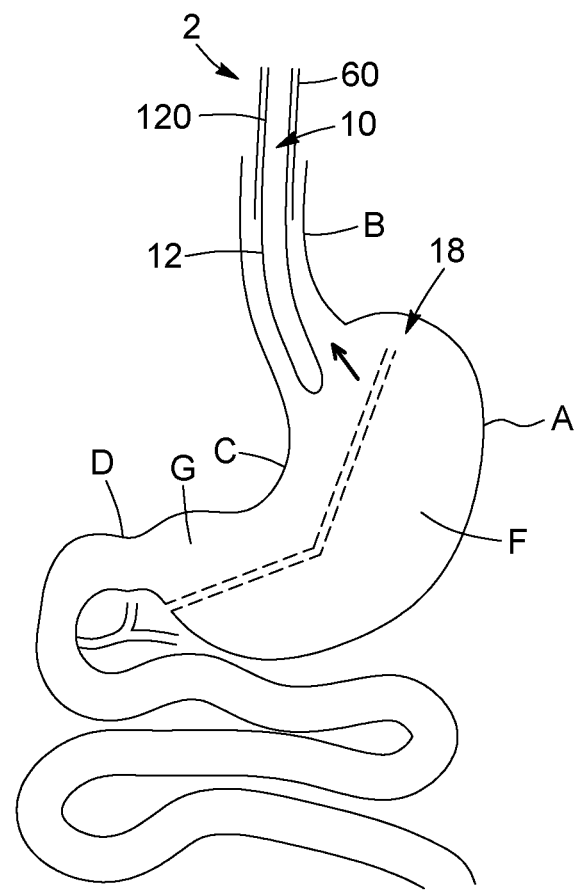
FIG. 9 is a schematic cross-sectional view of a stomach according to a fifth step of the sleeve gastroplasty method using the gastroplasty assembly.

Referring to FIGS. 8 and 9, once the sleeve (G) is formed, the method includes closing the extension member (14) into the retracted position along the segment (120). The method further includes translating the sheath (60) forward along the bougie (10) until the sheath (60) covers at least the segment (120) and the retracted extension member (14) (not seen in FIG. 9 when within the sheath (60)) to prevent the extension member from moving into the extended position.

Referring to FIG. 9, the method includes extracting the assembly (2) from the formed sleeve (G) while the sheath (60) keeps the extension member against the segment (120) of the elongated body (12) during displacement of the assembly along the sleeve (G) and oesophagus (B). The assembly (2) including the sheath (60) and the bougie (10) is further extracted from the oesophagus (B) without risking damaging any tissue or nerve during displacement because of an accidental splaying of the extension member.

As readily understood by one skilled in the art, the configuration of the extension member with respect to the bougie, and the positioning of the extension member in the extended position may differ from the ones illustrated in FIGS. 4 to 9, thereby leading to variations in the resulting junction line.

Figure 13:
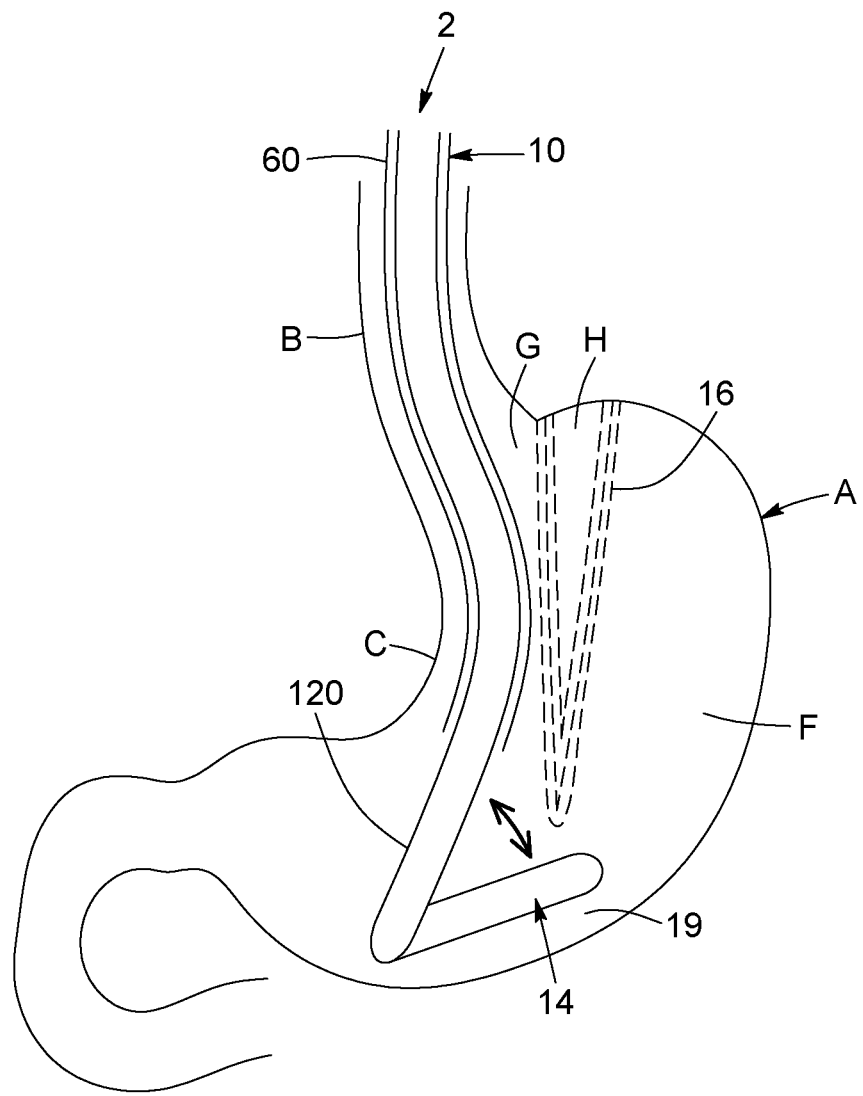
FIG. 13 is a schematic cross-sectional view of a stomach containing a gastroplasty assembly to form a sleeve and a bypass portion along a stapled V-shaped junction line.
Figure 14:
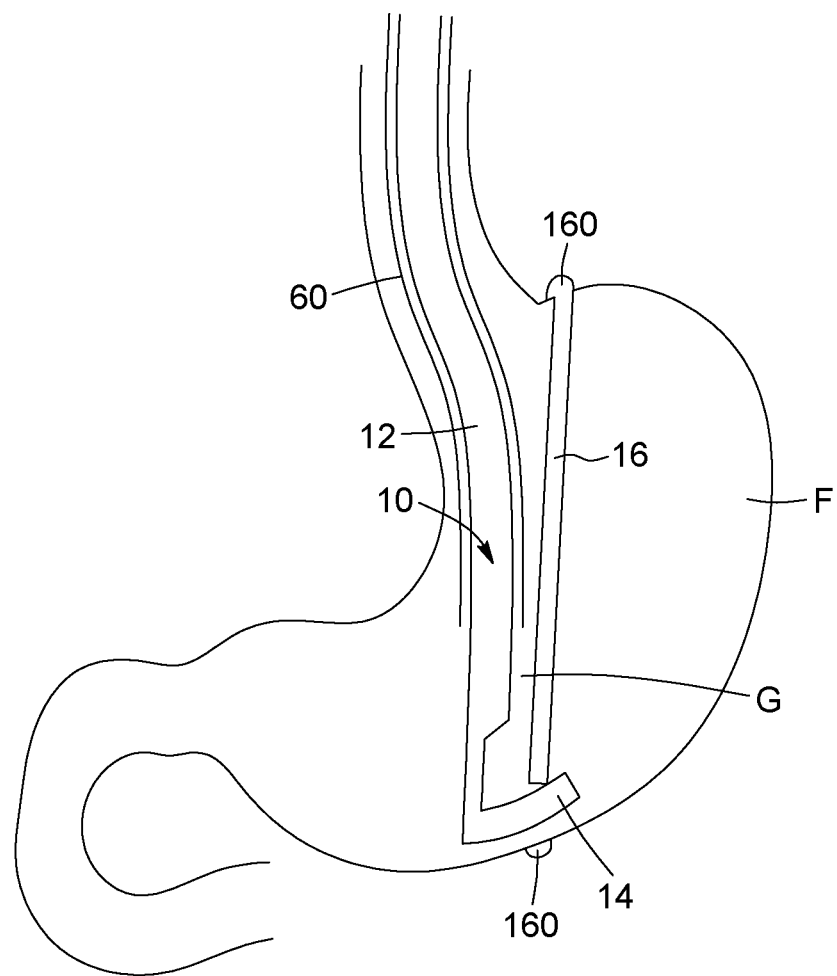
FIG. 14 is a schematic cross-sectional view of a stomach containing a gastroplasty assembly to form a sleeve and a bypass portion along to a clamped junction line.
Figure 17:
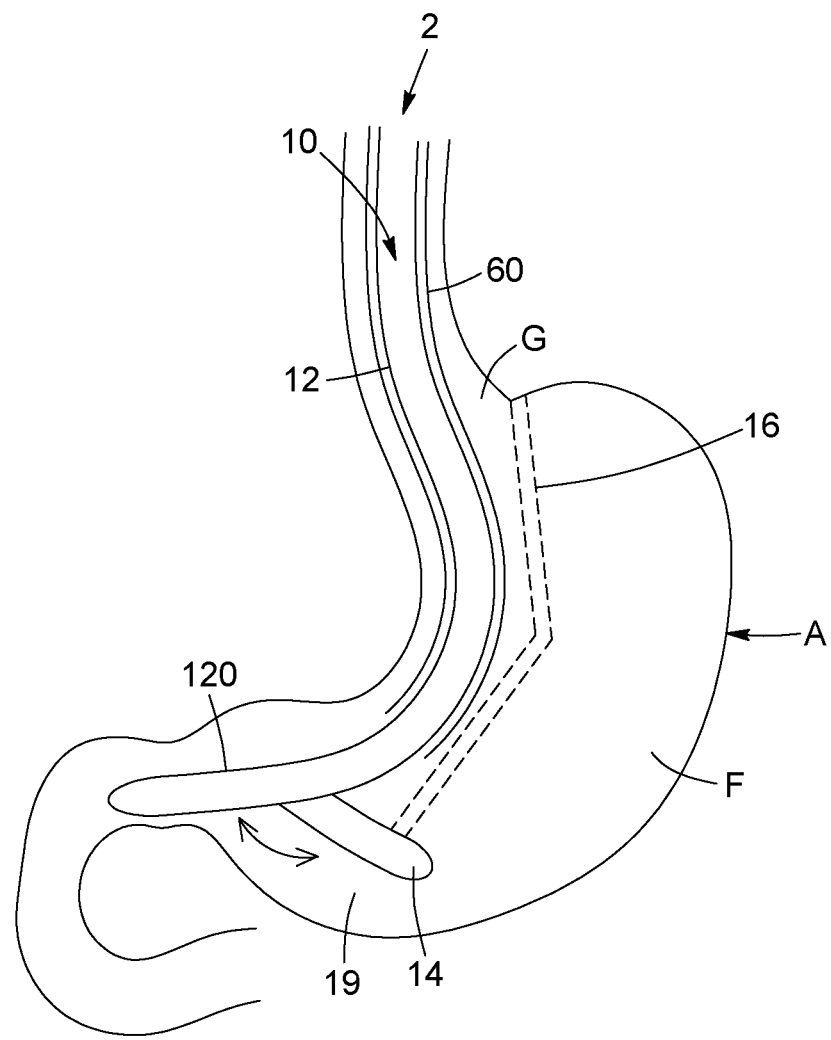
FIG. 17 is a schematic cross-sectional view of a stomach containing a gastroplasty assembly to form a sleeve and a bypass portion, the sleeve being open to the bypass portion of the stomach proximal to a gastro-duodenal junction thereof.

In some implementations, according to the type of gastroplasty which is performed, the sleeve may be opened to the bypassed portion of the stomach in a distal region thereof (instead of a proximal region as illustrated in FIGS. 4 to 9). As seen in FIGS. 13, 14 and 17, the method can include joining the stomach walls along an inner edge of the elongated body (120), opposite to the lesser curve (C), until reaching a distal portion of the extension member (14) in the extended position.

Referring to FIG. 13, the junction line (16) can be shaped as a V, such that a crotch of the V delimits the fluid passage (19) between the bypass portion of the stomach (F) and the sleeve (G). In this implementation, the distal portion of the extension member (14) is angled away from the gastroesophageal junction and positioned in a distal region of the stomach, with the extension member departing from a distal end of the elongated member (14), such that the opened bougie (10) has a general L-shape. The distal portion of the extension member serves to size the fluid passage (19) and prevents full joining of the stomach walls to leave a distal region of the sleeve (G) open in the distal region of the stomach proximate to the gastroduodenal junction. Optionally, the isolated portion (H) of the stomach may be separated from the sleeve by cutting a portion of the stomach along the junction line (16).

Optionally, as illustrated in FIG. 14, joining the opposed walls of the stomach along the bougie (10) can be performed with a clamping device (160). More specifically, the clamping device (160) can be used to clamp the stomach along the inner edge of the elongated body (12) to form the sleeve (G) and the bypass portion of the stomach (F). The clamping device (160) is configured to cooperate with the distal portion of the extension member (14) of the bougie (10) to leave the distal region of the sleeve (G) open, thereby ensuring fluid communication with the bypass portion of the stomach (F). Clamping forces are indeed exerted by the device (160) to form a junction line (16) which ends when encountering the extension member (14).

In another implementation illustrated in FIG. 17, the extension member (14) may extend at an angle away from segment (120) of the elongated body (12) with the extension member departing from the distal portion of the elongated member (14), such that the opened bougie (10) has a general T-shape. The method includes forming the sleeve (G) by stapling the opposed stomach walls along an inner edge of the elongated body (12) until reaching the extension member (14), the latter serving as a guide not to close the sleeve (G)

but rather delimiting a width of the fluid passage (19) between the bypassed portion (F) and the sleeve (G) in the distal region of the stomach, proximate to the gastroduodenal junction.

Consequently, the configuration of the extension member with respect to the elongated body and the sheath may therefore differ from what is illustrated in FIGS. 1 to 9, so as to provide an adequate guide according to variations in the junction line.

In some implementations, the sheath may be a tube extending along an entire length of the elongated body of the bougie, the sheath being displaceable along the bougie to uncover at least a portion of the elongated body of the bougie.

In other implementations, the sheath may be a tube segment positioned at a relevant location along the bougie, the tube segment being sized according to a corresponding segment of the elongated body from which the extension member departs at an angle away.

Figure 12:
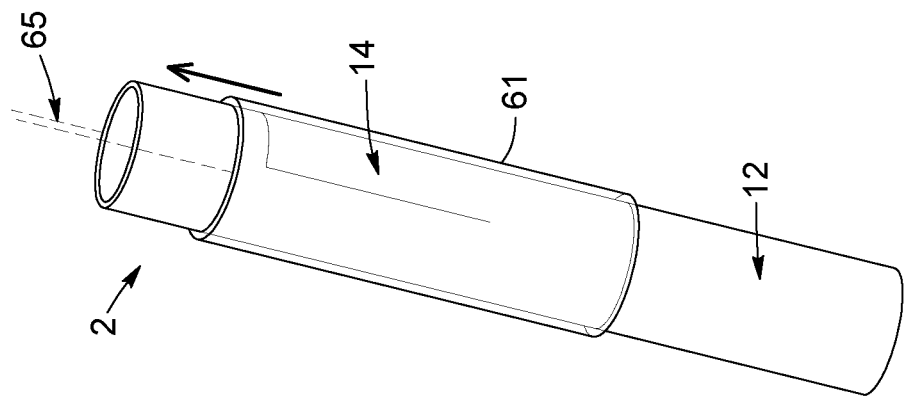
FIGS. 10 to 12 are schematic representations of a bougie and related sheath segments for performing a sleeve gastroplasty illustrating successive displacements of the sheath segments and extension member of the bougie.
Figure 11:
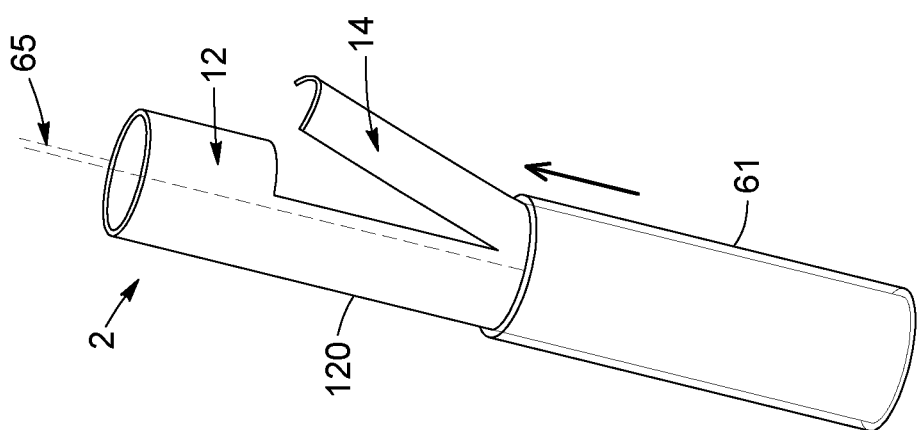
Figure 10:
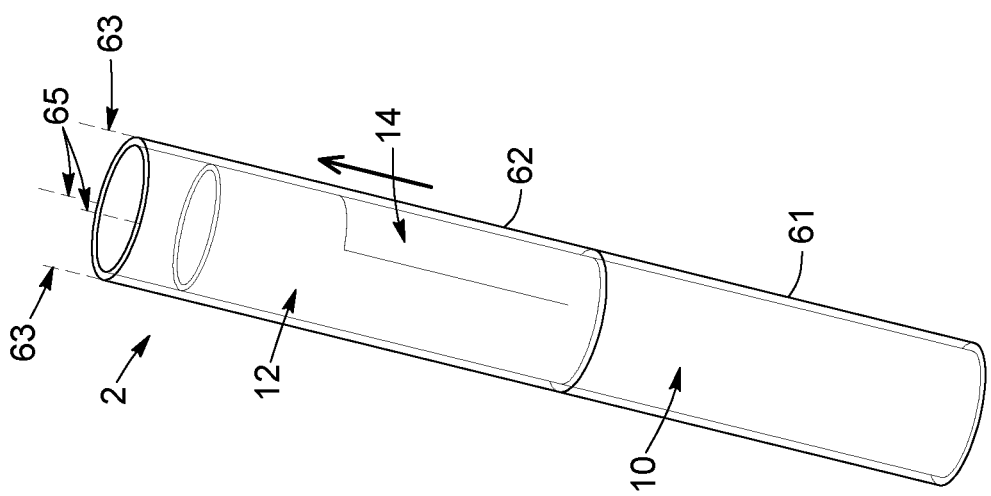

In other implementations, referring to FIGS. 10 to 12, the sheath may be configured as a two-part tube such that the sheath includes distal and proximal tube segments (61, 62). The distal and proximal tube segments (61, 62) are joined to prevent the extension member (14) from splaying during insertion of the bougie (10) within the stomach (not illustrated). The proximal tube (62) is then translated backward (see arrow in FIG. 10) to let the extension member (14) splay open and guide the surgeon during the sleeve gastroplasty (see FIG. 11). Once the sleeve is formed, the distal tube (61) is translated backward (see arrow in FIG. 11) to force the return of the extension member into the retracted position (see FIG. 12), thereby allowing for secure extraction of the assembly from the stomach. A wire system may be used, and one or more wires can be integrated within the distal and proximal tube walls such that a first set of wires (63) is pulled to actuate a backward translation of the proximal tube segment and a second set of wires (65) is pulled to actuate a backward translation of the distal tube segment.

Figure 15:
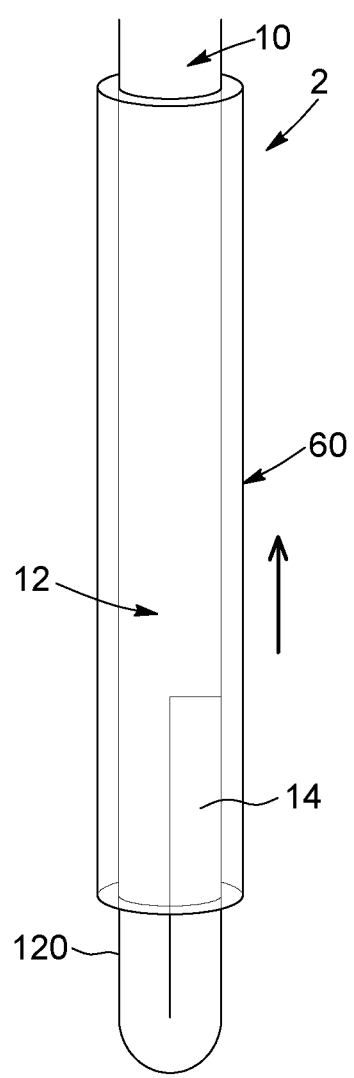
FIGS. 15 and 16 are schematic representations of a bougie and related sheath for performing a sleeve gastroplasty illustrating displacement of the sheath to release a distal extension member of the bougie (L-shaped structure).
Figure 16:
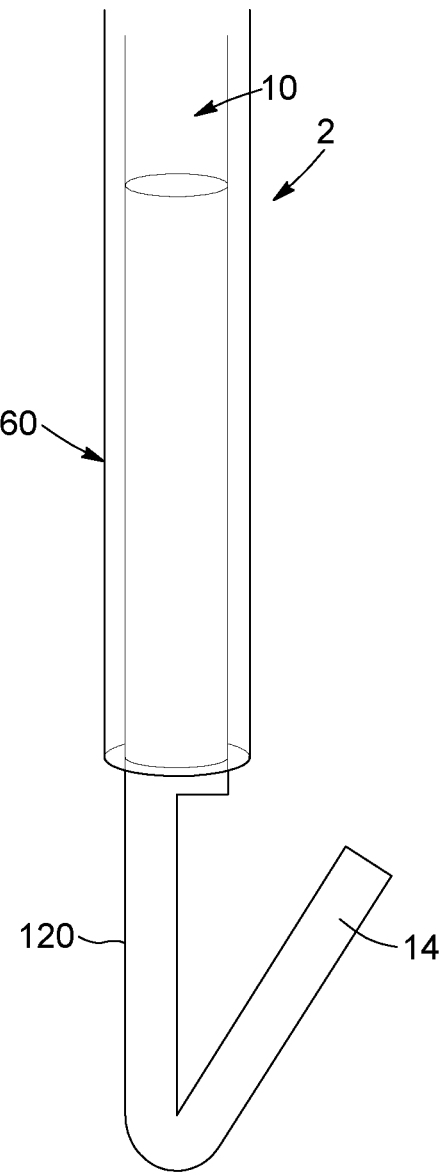

FIGS. 15 and 16 schematically illustrate the cooperation of the extension member (14) and the sheath (60) when the bougie (10) extends in a L-shape as seen in FIGS. 13 and 14. Backward translation (see arrow in FIG. 15) of the sheath (60) with respect to the bougie (10) uncovers segment (120) of the elongated body (12) to enable the release of the extension member (14) in the extended position. In this implementation, the extension member (14) may pivot with respect to segment (120) via a hinge (not illustrated) located about the distal end of the elongated body (12). Pivoting of the extension member about the hinge may be actuated via a wire system cooperating with a distal end of the extension member.

FIGS. 18 to 20 schematically illustrate the cooperation of the extension member (14) and the sheath (60) when the bougie (10) extends in a generally T-shape as seen on FIG. 17. Backward translation (see arrow in FIG. 18) of the sheath (60) with respect to the bougie (10) uncovers segment (120) of the elongated body (12) to enable the release of the extension member (14) in the extended position. In this implementation, both segment (120) and extension member (14) may be made of a resilient material naturally bending outwardly when unbiased as better seen in FIG. 19. Forward translation (see arrow in FIG. 20) enables to bias segment (120) and the extension member (14) towards each other so as to close the distal end of the elongated body (12). The assembly (2) may then be securely extracted from the stomach (not illustrated).

Figure 21:
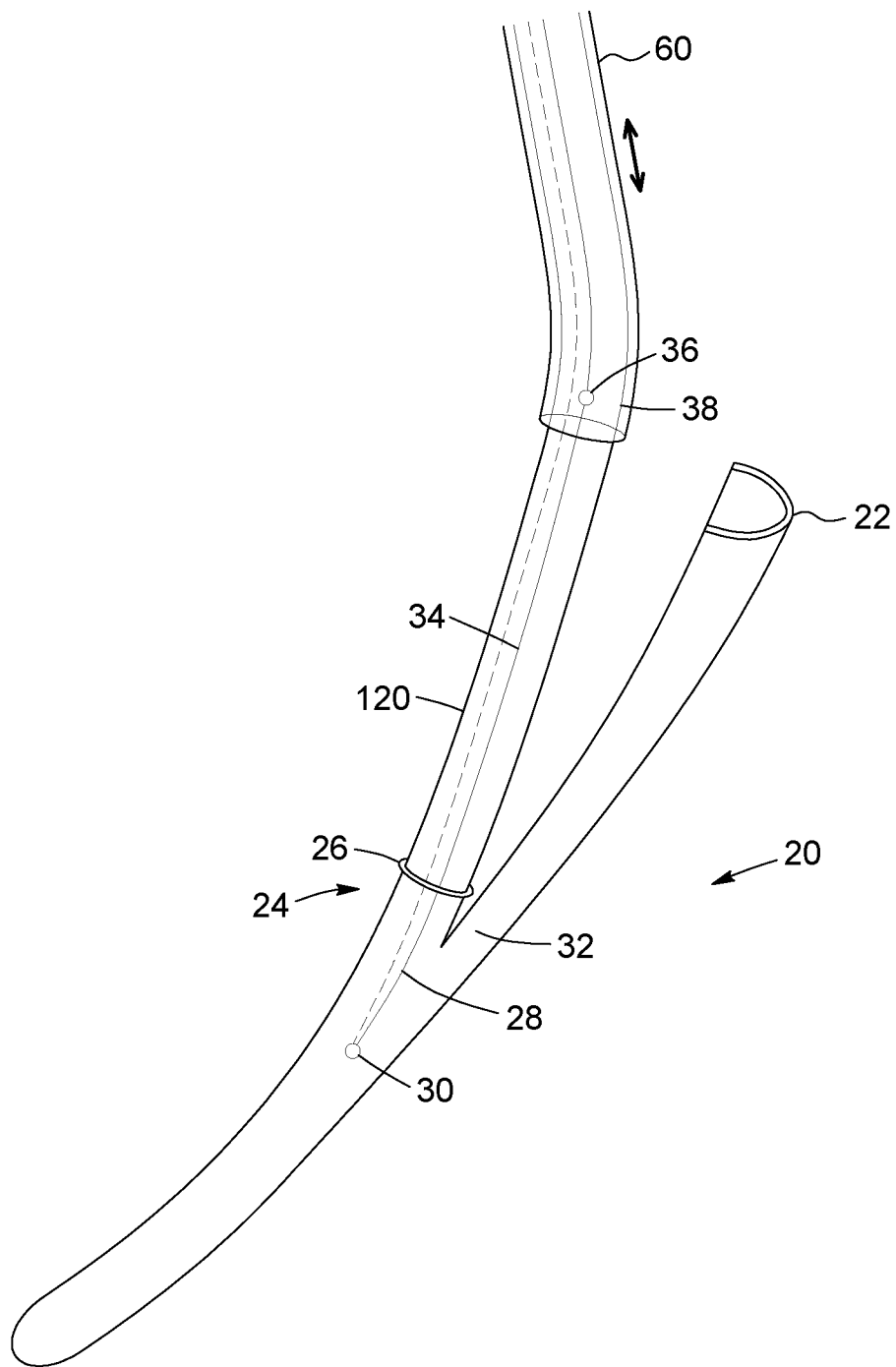
FIGS. 21 and 22 are schematic representations of a bougie and related sheath for performing a sleeve gastroplasty, the bougie including a ring and wire system to actuate movement of an extension member of the bougie.
Figure 22:
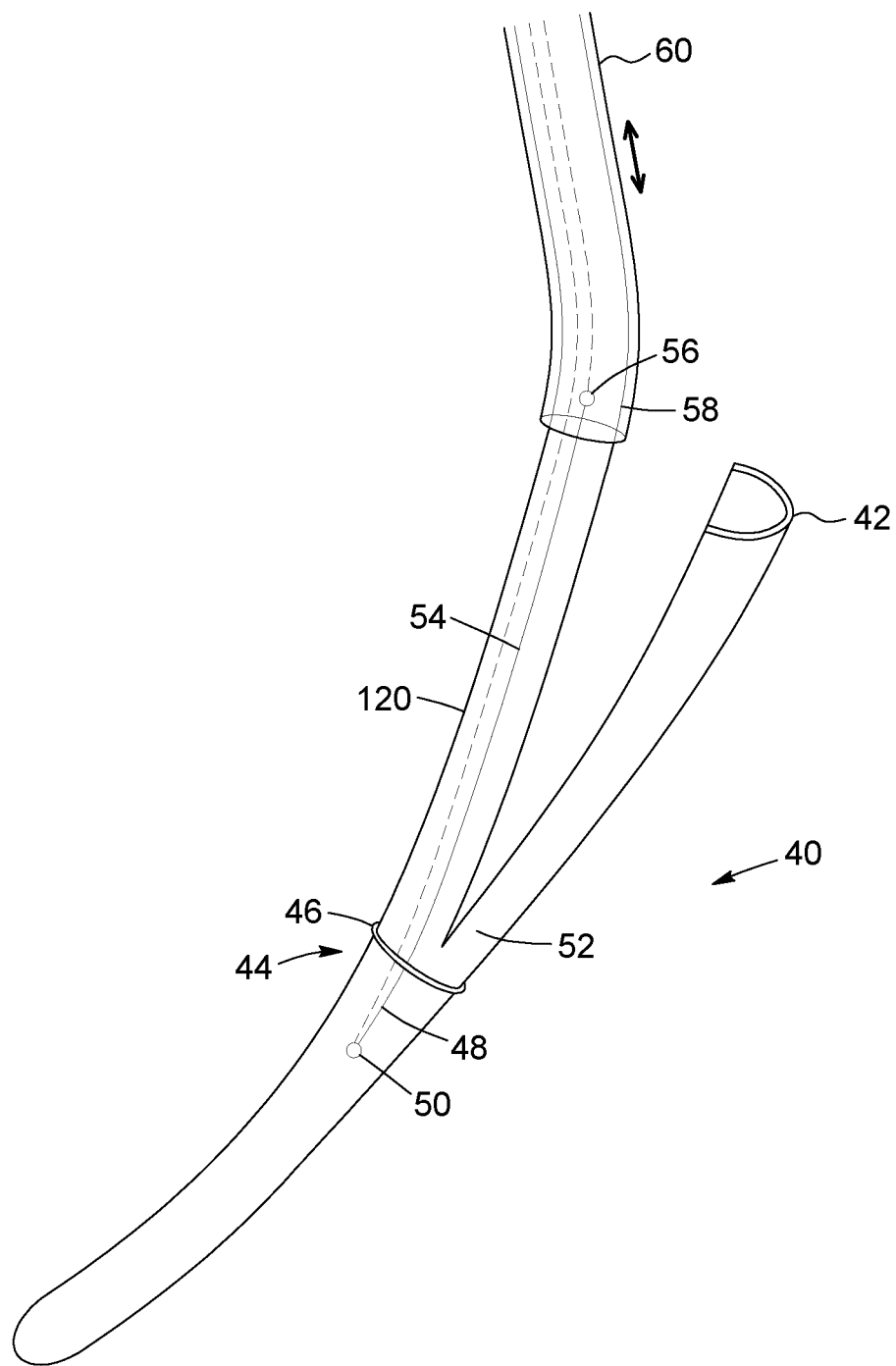

Various mechanisms can be used to reversibly move the extension member from the retracted position into the extended position. FIGS. 21 and 22 are provided as two exemplary implementations of an activation mechanism comprising a ring cooperating with wires.

Referring to FIG. 21, the bougie (20) is illustrated with the extension member (22) in the extended position. Once the sheath (60) is translated backward with respect to the bougie (20), the extension member (22) is uncovered and an activation mechanism (24) can be used to put the extension member (22) in the extended position. The activation mechanism (24) includes a sliding ring (26) that surrounds an external surface of the segment (120) of the bougie (20). An extending wire (28) passes through an internal lumen of the bougie (20) and exits the bougie (20) through an outlet port (30) located distally of a distal end (32) of the extension member (22). The extending wire (28) is then attached to the sliding ring (26). A retraction wire (34) is also routed from the sliding ring (26) through the internal lumen of the bougie (20), entering at an inlet port (36) located proximally of the proximal end (38) of the bougie (20). In operation, the extension member (22) is splayed open by pulling on the extending wire (28), thereby translating the sliding ring (26) forward and downwardly. The sliding ring (26) is wedged between the extension member (22) and the segment (120) of the bougie (20). The farther the sliding ring (26) is pulled toward the junction between the extension member (22) and the segment (120), the greater the angle between the two becomes. To put the extension member back into the retracted position, the retraction wire (34) is pulled, thereby moving the sliding ring (26) backward. The resilient nature of the extension member (22) brings it flush against the segment (120) of the bougie (20).

Another implementation of an activation mechanism is shown in FIG. 22. Alternatively from the implementation of FIG. 21, the extension member (42) may be biased open while being flexible enough to be held closed using the sliding ring (46) which is able to surround both segment (120) and extension member (42). An extending wire (48) passes through the internal lumen of the bougie (40) and exits the bougie through an outlet port (50) located distally of a distal end (52) of the extension member (42). The extending wire (48) is further attached to the sliding ring (46). A retraction wire (54) is routed from the sliding ring (46) into the internal lumen of the bougie (40), by entering the inlet port (56) located proximally of the proximal end (58) of the bougie (40). In operation, the extension member (42) is splayed open by pulling on the extending wire (48), thereby translating the sliding ring (46) forward along the bougie (40). Sliding of the ring (46) releases the extension member (42) which is free to splay open. One skilled in the art will understand that the farther the ring is downwardly moved along the bougie (40) toward the junction between the extension member (42) and the segment (120), the greater the angle at which the extension member extends becomes. To put the extension member back into the retracted position, the retraction wire (54) is pulled, thereby sliding the ring (46) backward in a proximal direction. Displacement of the sliding ring (46) collapses the extension member (42) against the segment (120) of the bougie (40).

For both implementations from FIGS. 21 and 22, the diameter of the sheath (60) is sized to accommodate for the sliding ring (26, 46). The sheath (60) is translated forward to contain the sliding ring (26, 46), segment (120) and the extension member (22, 42), thereby preventing the sliding ring (26, 46) from moving the extension member (22) into the extended position by accident during extraction of the bougie (20, 40) from the stomach (not illustrated in FIGS. 21 and 22).

Optionally, though not shown in the FIGS. 21 and 22, second extending and retraction wires may be similarly routed on an opposite side of the bougie such that when pulled, and equal force is applied to both sides of the sliding ring, thereby preventing the ring from hanging up on the bougie.

In some implementations, the assembly may include a light source visible through the walls of the stomach to provide further visible guidance to the surgeon when joining the stomach walls to form the sleeve.

The light source may include a plurality of light-emitting elements distributed along at least a portion of the bougie. The light-emitting elements may include led light bulbs embedded within the bougie, or apertures formed along an edge of the bougie and letting light from a light source to be visible for the practitioner. Optionally, the light-emitting elements may be distributed along an inner edge of both elongated body and extension member of the bougie to improve visibility of the junction line of the stomach.

Figure 23:
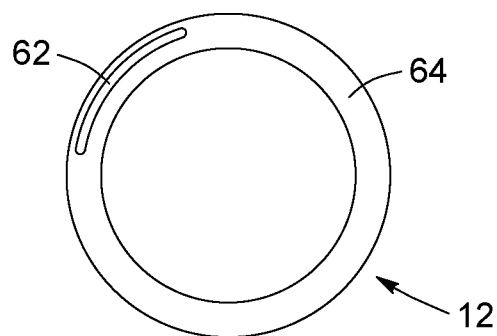
FIGS. 23 to 27 are schematic cross-sectional view of alternative implementations of a bougie including an air suction lumen.
Figure 24:
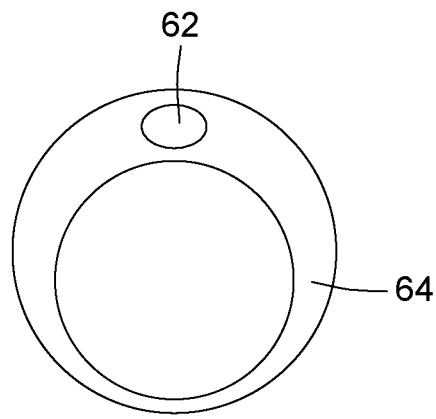
Figure 25:
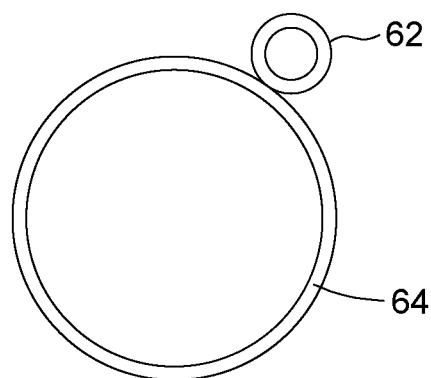
Figure 26:
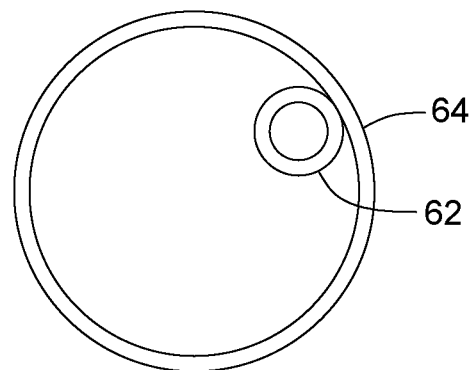
Figure 27:
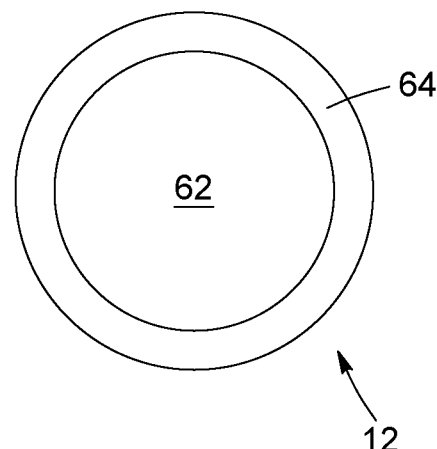
Figure 31:
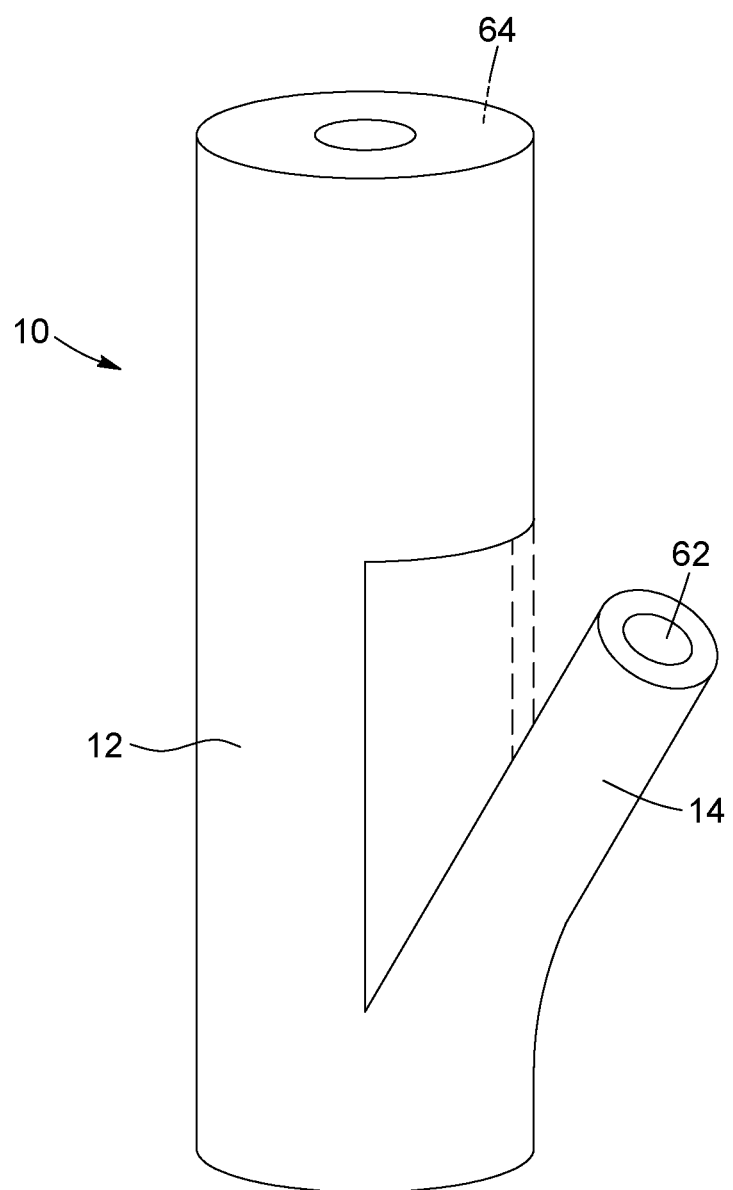
FIG. 31 is a schematic representation of a bougie and related sheath for performing a sleeve gastroplasty, the bougie including a tubular segment movable between a retracted position and an extended position when cooperating with the sheath.
Figure 32:
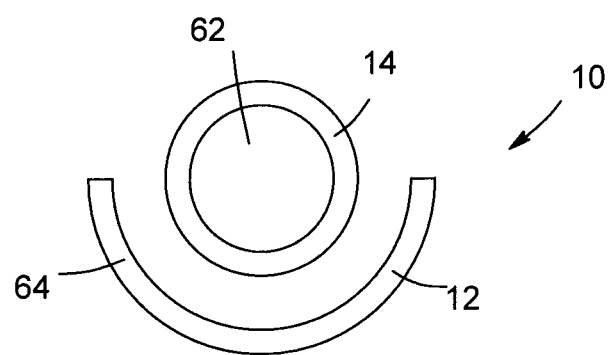
FIG. 32 is a schematic cross-sectional view of the bougie showing an opened tubular elongated body and the extendable tubular segment of the bougie of FIG. 31.

In some implementations, the bougie may further include a suction lumen being in fluid communication with the stomach cavity to suction any accumulation of fluids and forcing the stomach walls to collapse against the bougie, thereby making the bougie easier to visualize and follow. A suction source is connectable to the suction lumen to provide for suction power. The suction lumen extends along a length of the elongated body of the bougie, and suctions fluids from the stomach via at least one aperture formed in the elongated body. The at least one suction lumen (62) may be integral with a wall (64) of the elongated body (12) as seen in FIGS. 23 and 24, or may run along an inner or outer surface of the wall (64) of the elongated body (12) as seen in FIGS. 25 and 26. Optionally, the suction lumen (62) may also be formed by the inside lumen of the elongated body (12) itself as seen in FIG. 27. Further optionally, as seen in FIGS. 31 and 32, the extension member (14) itself can be tubular to form the suction lumen (62). In this implementation, the tubular extension member (14) is encased in the open lumen formed by the wall (64) of the elongated body (12) of the bougie (10) when in the retracted position.

In some implementations, the suction lumen may be in fluid communication with the stomach cavity via a plurality of apertures formed in the elongated body.

Figure 28:
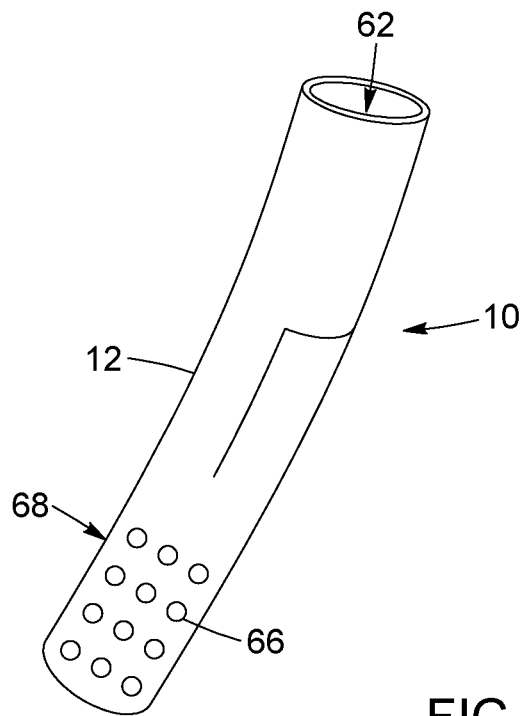
FIGS. 28 and 29 are schematic representations of a portion of a bougie including apertures in a distal region thereof.
Figure 29:
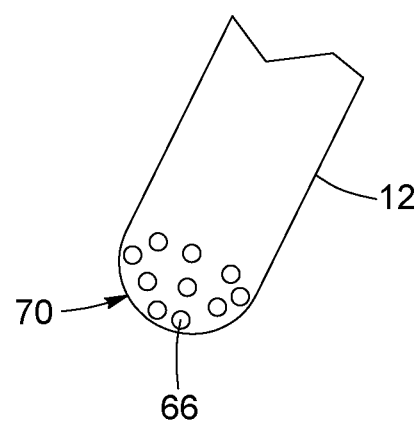
Figure 30:
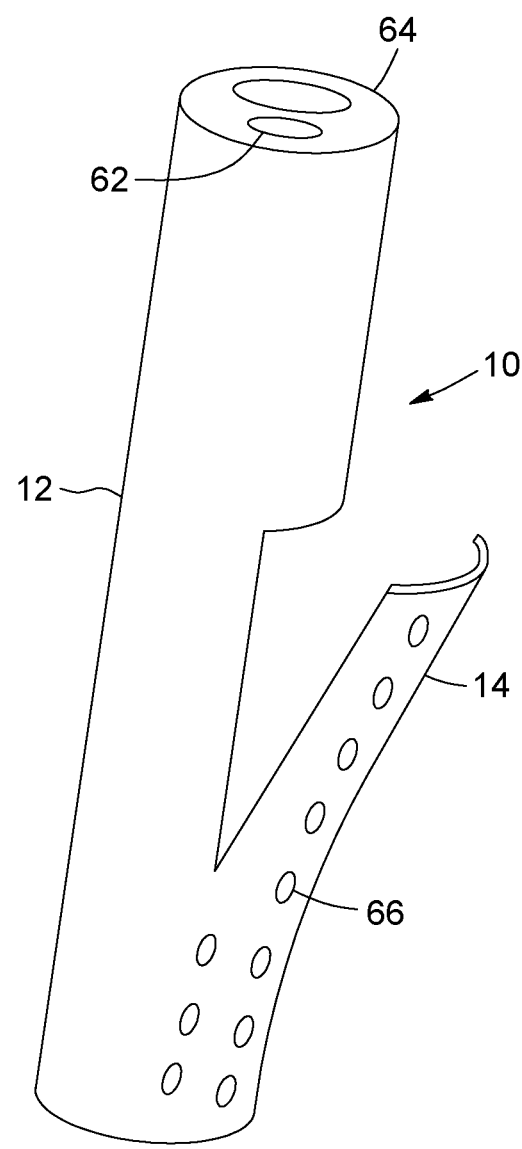
FIG. 30 is a schematic representation of a portion of a bougie including an air suction lumen and apertures along an extension member thereof.

Referring to FIG. 28, a distal portion (68) of the elongated body (12) may be provided with a plurality of apertures (66) ensuring fluid communication between a suction source and the stomach (not illustrated) via the suction lumen (62). Referring to FIG. 29, the apertures (66) may rather be provided at a distal end (70) of the elongated body (12). Referring to FIG. 30, the apertures (66) may be provided along an edge of the extension member (14) to provide enhanced suction where the junction line must end.

In some implementations, the bougie may further include a valve located in a proximal portion of the elongated body, the valve having an opening in fluid communication with the suction lumen previously described. The valve can act as an air vent or vent lumen to allow air to circulate within the suction lumen, thereby reducing or preventing stomach tissue from collapsing against and blocking the apertures of the suction lumen.

It should be noted that the sheath of the assembly is sized and shaped not to interfere with the apertures or valve communication with the suction lumen of the bougie.

It should be understood that any one of the above-mentioned optional aspects of the assembly and related method may be combined with any other of the aspects thereof, unless two aspects clearly cannot be combined due to their mutually exclusivity. For example, any of the structural elements of the assembly described herein-above, herein-below and/or in the appended Figures, may be combined with any of the general operational steps of the method for extraction and insertion of the assembly from and into the stomach.

Although the embodiments of the gastroplasty assembly and corresponding parts thereof consist of certain geometrical configurations as explained and illustrated herein, not all of these components and geometries are essential and thus should not be taken in their restrictive sense. It is to be understood, as also apparent to a person skilled in the art, that other suitable components and cooperation thereinbetween, as well as other suitable geometrical configurations, may be used for the assembly, as will be briefly explained herein and as can be easily inferred herefrom by a person skilled in the art. Moreover, it will be appreciated that positional descriptions such as "backward", "forward", "down", "up" and the like should, unless otherwise indicated, be taken in the context of the figures and should not be considered limiting.

The invention claimed is:

1. An assembly for use in performing a gastroplasty for dividing a stomach of a patient into a sleeve receiving food and a bypass portion, the assembly comprising:
  a bougie configured to enter the stomach, the bougie comprising:
    an elongated body having a segment being shaped to follow a lesser curve of the stomach, and
    an extension member having a proximal portion connected to the segment of the elongate body, the extension member being movable from a retracted position in which the extension member is generally aligned with the elongate body, to an extended position in which the extension member extends at an angle away from the segment within the stomach for positioning a distal portion of the extension member away from a gastroesophageal junction of the stomach; and
  a sheath having an elongated main lumen in which the bougie is inserted, the sheath being translatable along the bougie between:
    a first position in which the sheath at least covers the extension member of the bougie for maintaining the extension member in the retracted position, and
    a second position in which the sheath is staggered with respect to the extension member for allowing the extension member to move from the retracted position into the extended position.

2. The assembly of claim 1, comprising an actuator which is configured to displace the sheath between the first position and the second position along the bougie.

3. The assembly of claim 2, wherein the actuator is a wire system comprising at least one wire which is pullable to actuate translation of the sheath with respect to the bougie.

4. The assembly of claim 1, comprising an activation mechanism which is configured to move the extension member from at least one of the retracted position and the extended position into to the other position.

5. The assembly of claim 4, wherein the activation mechanism is a wire system comprising at least one wire which is pullable to actuate movement of the extension member with respect to the segment of the elongated body.

6. The assembly of claim 4, wherein the activation mechanism comprises a magnet located in a distal portion of the extension member, the extension member being movable from outside the stomach under the action of a secondary magnet.

7. The assembly of claim 1, wherein a distal portion of the extension member is a free-end that is spaced-away from a proximal portion of the segment to define a Y-shape when the extension member is in the extended position.

8. The assembly of claim 1, wherein a distal portion of the extension member is a free-end that is spaced-away from a distal portion of the segment to define a T-shape when the extension member is in the extended position.

9. The assembly of claim 1, wherein a distal portion of the extension member is a free-end that is spaced-away from a distal end of the segment to define a L-shape when the extension member is in the extended position.

10. The assembly of claim 1, wherein the sheath has a proximal portion made of a first material and a distal portion made of a second material, the second material having an enhanced rigidity in comparison to the first material, said distal portion enclosing the extension member of the bougie in the retracted position when the sheath is in the first position.

11. The assembly of claim 1, wherein the bougie further comprises a suction lumen extending along the elongated body, the suction lumen being connectable to a suction source and being in fluid communication with the stomach cavity via at least one aperture of the elongated body.

12. The assembly of claim 11, further comprising an air valve having an opening in fluid communication with the suction lumen, the valve being connected to a proximal portion of the elongated body.

13. The assembly of claim 1, further comprising a plurality of light-emitting elements distributed along at least a portion of the bougie to provide further visible guidance when joining the stomach walls to form the sleeve.

14. The assembly of claim 1, wherein the sheath comprises distal and proximal tube segments, the proximal tube segment being translatable with respect to the bougie in a backward direction to release the extension member in the extended position, and the distal tube segment being translatable with respect to the bougie in a forward direction to close the extension member in the retracted position.

15. A kit for performing a gastroplasty dividing a stomach of a patient into a sleeve receiving food and a bypass portion, the kit comprising:

a bougie configured to enter the stomach, the bougie comprising:
   an elongated body having a segment being shaped to follow a lesser curve of the stomach, and
   an extension member having a proximal portion connected to the segment of the elongate body, the extension member being movable from a retracted position in which the extension member is generally aligned with the elongate body, to an extended position in which the extension member extends at an angle away from the segment within the stomach for positioning a distal portion of the extension member away from a gastroesophageal junction of the stomach; and
a sheath having an elongated main lumen in which the bougie is slidably insertable, the sheath being translatable along the bougie between:
   a first position in which the sheath at least covers the extension member of the bougie for maintaining the extension member in the retracted position, and
   a second position in which the sheath is staggered with respect to the extension member for allowing the extension member to move from the retracted position into the extended position.

16. The kit of claim 15, comprising an actuator which is configured to displace the sheath between the first position and the second position along the bougie.

17. The kit of claim 15, comprising an activation mechanism which is configured to move the extension member from at least one of the retracted position and the extended position into to the other position.

18. The kit of claim 15, wherein the bougie further comprises a suction lumen extending along the elongated body, the suction lumen being connectable to a suction source and being in fluid communication with at least one aperture of the elongated body.

19. The kit of claim 18, wherein the elongated body is provided with a plurality of apertures located in a distal portion of the elongated body to allow fluid passage from the stomach into the suction lumen when a suction power is applied.

20. The kit of claim 15, further comprising a plurality of light-emitting elements positionable along at least a portion of the bougie to provide further visible guidance when joining the stomach walls to form the sleeve.

* * * * *